United States Patent
Tanaka et al.

(10) Patent No.: US 10,456,106 B2
(45) Date of Patent: Oct. 29, 2019

(54) ULTRASONIC DIAGNOSTIC APPARATUS, MEDICAL IMAGE PROCESSING APPARATUS, AND MEDICAL IMAGE PROCESSING METHOD

(71) Applicant: TOSHIBA MEDICAL SYSTEMS CORPORATION, Otawara-Shi, Tochigi-Ken (JP)

(72) Inventors: Go Tanaka, Otawara (JP); Kazutoshi Sadamitsu, Otawara (JP); Koichiro Kurita, Nasushiobara (JP); Eiji Goto, Otawara (JP); Itsuki Kuga, Nasushiobara (JP); Junho Cha, Busan (KR)

(73) Assignee: TOSHIBA MEDICAL SYSTEMS CORPORATION, Otawara-Shi (JP)

(*) Notice: Subject to any disclaimer, the term of this patent is extended or adjusted under 35 U.S.C. 154(b) by 436 days.

(21) Appl. No.: 13/715,687

(22) Filed: Dec. 14, 2012

(65) Prior Publication Data

US 2013/0102903 A1 Apr. 25, 2013

Related U.S. Application Data

(63) Continuation of application No. PCT/JP2012/070088, filed on Aug. 7, 2012.

(30) Foreign Application Priority Data

Aug. 19, 2011 (JP) ................... 2011-179613
Aug. 2, 2012 (JP) ................... 2012-172250

(51) Int. Cl.
*A61B 8/14* (2006.01)
*A61B 8/08* (2006.01)
*A61B 8/00* (2006.01)

(52) U.S. Cl.
CPC ............ *A61B 8/145* (2013.01); *A61B 8/08* (2013.01); *A61B 8/085* (2013.01); *A61B 8/0891* (2013.01);
(Continued)

(58) Field of Classification Search
None
See application file for complete search history.

(56) References Cited

U.S. PATENT DOCUMENTS 6,167,296 A 12/2000 Shahidi
6,500,118 B1 * 12/2002 Hashimoto ............ A61B 8/00
128/916

(Continued)

FOREIGN PATENT DOCUMENTS

CN 101779969 A 7/2010
JP 2002-510230 A 4/2002
(Continued)

OTHER PUBLICATIONS

International Search Report (JP) dated Sep. 4, 2012 for corresponding International Application No. PCT/JP2012/070088.

(Continued)

*Primary Examiner* — Thomas J Hong
*Assistant Examiner* — Shahdeep Mohammed
(74) *Attorney, Agent, or Firm* — Kenichiro Yoshida

(57) ABSTRACT

According to one embodiment, a position detection unit detects position information of an ultrasonic probe including ultrasonic transducers, with reference to a reference position. A transmission/reception unit supplies a driving signal to each transducer and generates a reception signal based on a reception echo signal generated by the transducer. Based on the reception signal, a three-dimensional data generation unit generates first three-dimensional data, in which a region corresponding to a living body tissue is specified by a (Continued)

specifying unit. A setting unit sets a first viewpoint based on the position information and specified region. An image generation unit generates a rendering image by rendering processing using the first viewpoint and first three-dimensional data.

20 Claims, 11 Drawing Sheets

(52) U.S. Cl.
CPC .......... *A61B 8/4245* (2013.01); *A61B 8/4254* (2013.01); *A61B 8/4444* (2013.01); *A61B 8/4488* (2013.01); *A61B 8/466* (2013.01); *A61B 8/469* (2013.01); *A61B 8/483* (2013.01); *A61B 8/523* (2013.01); *A61B 8/5207* (2013.01); *A61B 8/5246* (2013.01)

(56) References Cited

U.S. PATENT DOCUMENTS

| | | | |
|---|---|---|---|
| 7,167,180 B1* | 1/2007 | Shibolet | G06T 7/13 345/418 |
| 8,285,011 B2* | 10/2012 | Chen | G06T 7/0012 382/128 |
| 2005/0090746 A1* | 4/2005 | Ohtake | 600/447 |
| 2005/0256402 A1* | 11/2005 | Kawashima et al. | 600/437 |
| 2006/0253032 A1* | 11/2006 | Altmann et al. | 600/466 |
| 2008/0085042 A1 | 4/2008 | Trofimov et al. | |
| 2008/0287803 A1* | 11/2008 | Li et al. | 600/466 |
| 2009/0060298 A1* | 3/2009 | Weijers | G06T 7/0012 382/128 |
| 2009/0306508 A1* | 12/2009 | Yoshida et al. | 600/443 |
| 2010/0185094 A1 | 7/2010 | Hamada et al. | |
| 2011/0018871 A1* | 1/2011 | Shirahata | A61B 8/00 345/419 |
| 2012/0113111 A1* | 5/2012 | Shiki | A61B 8/08 345/419 |

FOREIGN PATENT DOCUMENTS

| | | |
|---|---|---|
| JP | 2008-136850 A | 6/2008 |
| JP | 2009-125394 A | 6/2009 |
| JP | 2011-156086 A | 8/2011 |
| WO | WO2011001938 A1 * | 6/2011 |

OTHER PUBLICATIONS

Chinese Office Action with its English translation for Chinese Patent Application No. 201280001326.5 dated May 4, 2014.

English Translation of International Search Report (JP) dated Sep. 4, 2012 for corresponding International Application No. PCT/JP2012/070088.

* cited by examiner

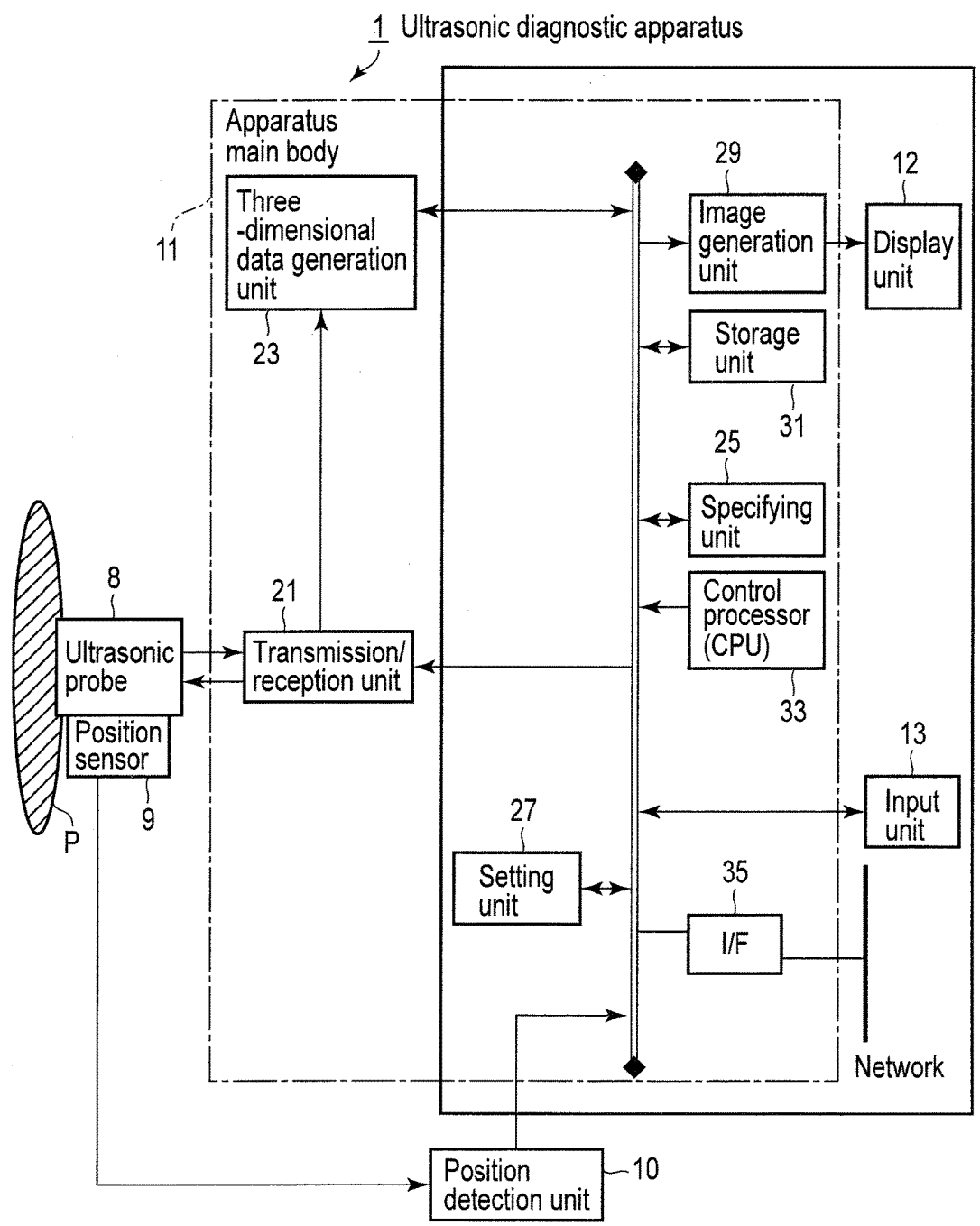
F I G. 1

ULTRASONIC DIAGNOSTIC APPARATUS, MEDICAL IMAGE PROCESSING APPARATUS, AND MEDICAL IMAGE PROCESSING METHOD

CROSS REFERENCE TO RELATED APPLICATIONS

This application is a Continuation Application of PCT Application No. PCT/JP2012/070088, filed Aug. 7, 2012 and based upon and claiming the benefit of priority from Japanese Patent Applications No. 2011-179613, filed Aug. 19, 2011; and No. 2012-172250, filed Aug. 2, 2012, the entire contents of all of which are incorporated herein by reference.

FIELD

Embodiments described herein relate generally to an ultrasonic diagnostic apparatus which generates rendering images, a medical image processing apparatus, and a medical image processing method.

BACKGROUND

Recently, there has been commercially available an ultrasonic diagnostic apparatus which acquires echo signals from an object by three-dimensionally scanning the object. This ultrasonic diagnostic apparatus can generate and display a three-dimensional image (for example, a rendering image) by generating three-dimensional data based on echo signals. To generate a three-dimensional image, this apparatus executes, for example, rendering processing (for example, volume rendering or surface rendering) for three-dimensional data. A viewpoint, line of sight, visual angle, projection region, and the like used for rendering processing are set for three-dimensional data. After the above setting, the apparatus generates a rendering image (for example, a parallel projection image or a perspective projection image) by executing parallel projection or perspective projection.

As one application example of a rendering image display method, there is available a display method of continuously moving the viewpoint set in an organ and consecutively displaying rendering images corresponding to the moved viewpoint. In this display method, for example, when handling three-dimensional data concerning an organ having a luminal form (to be referred to as a luminal organ hereinafter), a viewpoint is set in the lumen of the luminal organ. A line of sight is set in the extending direction of the lumen with the set viewpoint being a start point. In addition, a predetermined visual angle centered on the set viewpoint is set. The apparatus then executes perspective projection by using the set viewpoint, line of sight, and visual angle. The viewpoint is moved along the lumen in accordance with operation by the operator or at a predetermined velocity. Moving this viewpoint makes it possible to display an image of the interior of the lumen. This display method allows the operator to thoroughly observe the inner wall of the lumen.

As shown in, for example, FIG. 13, however, when the apparatus generates three-dimensional data after moving an ultrasonic probe, the viewpoint in this display method is located at a position fixed on a coordinate system concerning the three-dimensional data regardless of the position of the ultrasonic probe. This raises a problem that when a viewpoint is moved accompanying the movement of the ultrasonic probe, the position of the moved viewpoint may fall outside the interior or the lumen. When this happens, no perspective projection image of the interior of the lumen to be observed is displayed. In addition, assume that the apparatus has generated three-dimensional data by using a mechanical four-dimensional probe designed to execute three-dimensional scanning by swinging a one-dimensional array in a direction perpendicular to the array direction of a plurality of transducers. In this case, when the apparatus executes this display method, the frame rate is insufficient in continuous, real-time display of rendering images.

BRIEF DESCRIPTION OF THE DRAWINGS

FIG. 1 is a block diagram showing the arrangement of an ultrasonic diagnostic apparatus according to this embodiment.

DETAILED DESCRIPTION

Figure 2:
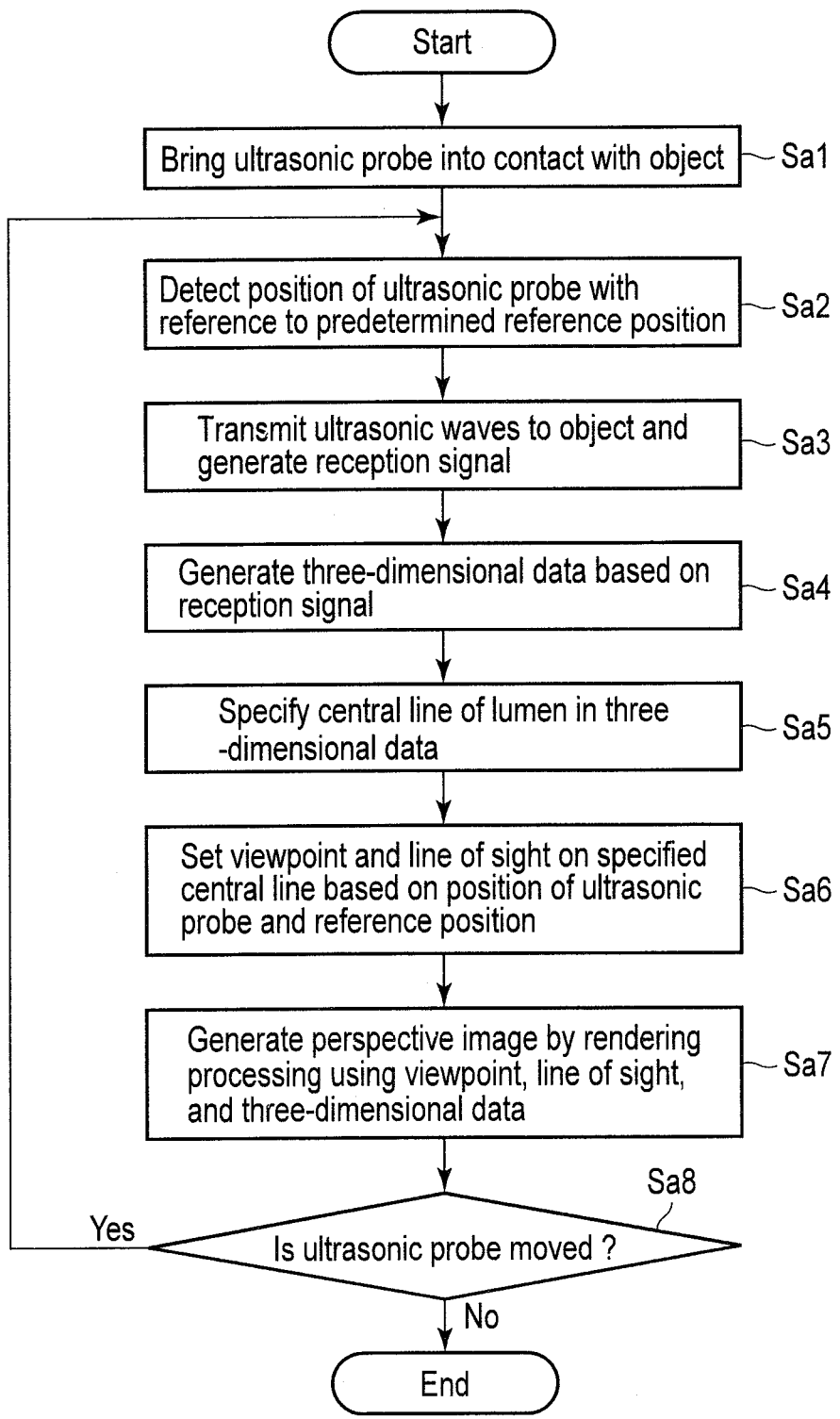
FIG. 2 is a flowchart showing a procedure for the processing of setting a viewpoint and a line of sight in a luminal region and generating a perspective projection image according to this embodiment.

In general, according to one embodiment, an ultrasonic diagnostic apparatus includes an ultrasonic probe, a position detection unit, a transmission/reception unit, a three-dimensional data generation unit, a specifying unit, a setting unit, and an image generation unit.

The ultrasonic probe includes a plurality of ultrasonic transducers.

The position detection unit is configured to detect position information of the ultrasonic probe with reference to a predetermined reference position.

The transmission/reception unit is configured to supply a driving signal to each of the ultrasonic transducers and generate a reception signal based on each reception echo signal generated by each of the ultrasonic transducers.

The three-dimensional data generation unit is configured to generate first three-dimensional data based on the reception signal;

The specifying unit is configured to specify a region corresponding to a living body tissue in the first three-dimensional data.

The setting unit is configured to set a first viewpoint based on the position information and the specified region.

The image generation unit is configured to generate a rendering image by rendering processing using the set first viewpoint and the first three-dimensional data.

An ultrasonic diagnostic apparatus according to this embodiment will be described below with reference to the accompanying drawing. Note that the same reference numerals in the following description denote constituent elements having almost the same functions and arrangements, and a repetitive description will be made only when required.

FIG. 1 is a block diagram of an ultrasonic diagnostic apparatus 1 according to this embodiment. As shown in FIG. 1, the ultrasonic diagnostic apparatus 1 includes an ultrasonic probe 8, a position sensor 9, a position detection unit 10, an apparatus main body 11, a display unit 12, and an input unit 13 which is connected to the apparatus main body 11 to input various kinds of commands, instructions, and information from the operator to the display unit 12. In addition; a biological signal measurement unit (not shown) typified by an electrocardiograph, phonocardiograph, sphygmograph, or respiration sensor and a network may be connected to the ultrasonic diagnostic apparatus 1 via an interface unit (to be referred to as an I/F hereinafter) 35.

The ultrasonic probe 8 includes piezoelectric transducers as lossless acoustic/electric conversion elements such as piezoelectric ceramic elements. A plurality of piezoelectric transducers are juxtaposed and mounted on the distal end of the ultrasonic probe 8. Assume that in the following description, one piezoelectric transducer forms one channel. Each piezoelectric transducer generates an ultrasonic wave in response to a driving signal supplied from a transmission/reception unit 21 (to be described later). Each piezoelectric transducer generates a reception echo signal in response to the reception of an ultrasonic wave (to be referred to as an echo signal hereinafter) reflected by a living tissue of an object. The ultrasonic probe 8 will be described below as a mechanical four-dimensional probe which executes three-dimensional scanning by swinging a one-dimensional array in a direction perpendicular to the array direction of a plurality of transducers. Note that the ultrasonic probe 8 is not limited to a mechanical four-dimensional probe, and it is possible to use a two-dimensional array probe.

Note that the ultrasonic probe 8 may be a one-dimensional array probe having a plurality of transducers arrayed one-dimensionally. In this case, the operator implements three-dimensional scanning by swinging or translating the probe in a direction perpendicular to the array direction of the transducers. When, for example, the operator swings the one-dimensional array probe, the position detection unit 10 (to be described later) detects the swinging direction of the one-dimensional array probe. With this operation, a three-dimensional data generation unit 23 generates three-dimensional data (to be described later) by using B-mode data of each of a plurality of slices respectively corresponding to a plurality of swing angles of the one-dimensional array probe and the swing angles and probe positions detected by the position detection unit 10 (to be described later). As described above, even using a one-dimensional array probe allows to generate three-dimensional data (to be described later). Even when the operator translates the one-dimensional array probe, the apparatus can perform the operation of generating three-dimensional data by combining B-mode data based on probe positions in the same manner as described above.

The position sensor 9 acquires the positional information of the ultrasonic probe 8 (to be also referred to as probe position information hereinafter) with reference to a predetermined reference position. Probe position information includes the position of the ultrasonic probe 8 relative to the predetermined reference position and the angle of the ultrasonic probe 8. The angle of the ultrasonic probe 8 is the inclination of the ultrasonic probe 8 relative to a predetermined reference direction. The predetermined reference position is, for example, the position of the apparatus main body 11 of the ultrasonic diagnostic apparatus 1. For example, the predetermined reference direction is defined by three orthogonal axes. The position sensor 9 is provided on, for example, the ultrasonic probe 8. The position sensor 9 outputs acquired probe position information to the position detection unit 10 (to be described later).

The position sensor 9 is, for example, a magnetic sensor, infrared sensor, angle sensor, or angular velocity sensor (e.g., a gyro sensor). For example, the magnetic sensor acquires probe position information with reference to a predetermined reference position by using the magnetism transmitted from a magnetic transmitter (not shown) in the position detection unit 10 (to be described later). The infrared sensor acquires probe position information with reference to the predetermined reference position by using the infrared rays transmitted from an infrared transmitter (not shown) in the position detection unit 10 (to be described later). Note that more commonly used electromagnetic waves may be used instead of infrared rays. Note that if the position sensor 9 is a magnetic sensor, a reference position may the position of the magnetic transmitter. In addition, if the position sensor 9 is an infrared sensor, a reference position may be the position of the infrared transmitter. It is possible to properly adjust a reference position in accordance with an instruction from the operator via the input unit 13 (to be described later). Note that predetermined reference position may be a position at which the probe comes into contact with the body surface of the object for the first time.

The angle sensor detects the angle of the ultrasonic probe 8 relative to the body surface of an object. The angular velocity sensor detects an angular velocity corresponding to the movement of the ultrasonic probe 8. An output from an angle sensor or an acceleration sensor in the position sensor 9 is called angle information. Note that angle information may be decided based on the positions of two points output from two magnetic sensors, two infrared sensors, or a combination of a magnetic sensor and an infrared sensor provided on a side surface of the ultrasonic probe 8.

The position detection unit 10 detects the position and inclination of the ultrasonic probe 8 with reference to a predetermined reference position by using the probe position information output from the position sensor 9. More specifically, the position detection unit 10 decides the position of the ultrasonic probe 8 on an absolute coordinate system with reference to the predetermined reference position. The position of the ultrasonic probe 8 on the absolute coordinate system will be referred to as probe coordinates hereinafter. The position detection unit 10 outputs probe coordinates to a three-dimensional data generation unit 23, a specifying unit 25, a setting unit 27, and the like (which will be described later).

The position detection unit 10 updates position information in accordance with the movement of the ultrasonic probe 8. Alternatively, the position detection unit 10 updates position information at predetermined time intervals (for example, 60 times/sec).

The apparatus main body 11 includes the transmission/reception unit 21, the three-dimensional data generation unit 23, the specifying unit 25, the setting unit 27, an image generation unit 29, a storage unit 31, a control processor (to be referred to as a CPU (Central Processing Unit)) 33, and the I/F 35.

The transmission/reception unit 21 includes a trigger generation circuit, transmission delay circuit, pulser circuit, preamplifier circuit, analog to digital (to be referred to as A/D hereinafter) converter, reception delay circuit, and adder (none of which are shown). The trigger generation circuit repeatedly generates rate pulses for the formation of transmission ultrasonic waves at a predetermined rate frequency. The trigger generation circuit repeatedly generates rate pulses at a rate frequency of, for example, 5 kHz. These rate pulses are distributed to channel counts and sent to the transmission delay circuit. The transmission delay circuit gives each rate pulse a delay time necessary to focus an ultrasonic wave into a beam and determine transmission directivity for each channel. The pulser circuit applies a voltage pulse (driving signal) to each transducer of the ultrasonic probe 8 at the timing based on this rate pulse, thereby transmitting ultrasonic beams to the object.

The apparatus receives the echo signal reflected by the living tissue of the object as a reception echo signal via the ultrasonic probe 8 for each channel. The preamplifier circuit amplifies the reception echo signal received from the object via the ultrasonic probe 8 for each channel. The A/D converter converts each amplified reception echo signal into a digital signal. The reception delay circuit gives the echo signals converted into digital signals delay times required to determine reception directivity. The adder adds a plurality of echo signals given the delay times. With this addition, the transmission/reception unit 21 generates a reception signal with a reflection component from a direction corresponding to the reception directivity being enhanced. The transmission directivity and the reception directivity determine the overall directivity of ultrasonic transmission/reception (which in turn determines so-called "ultrasonic scanning lines"). The transmission/reception unit 21 outputs a reception signal for each depth on each scanning line in a scanned region to the three-dimensional data generation unit 23 (to be described later). Note that the transmission/reception unit 21 may have a parallel reception function of simultaneously receiving echo signals generated on a plurality of scanning lines by one ultrasonic transmission.

The three-dimensional data generation unit 23 includes a B-mode data generation unit (not shown). Note that the three-dimensional data generation unit 23 may include a color/Doppler unit (not shown) which generates three-dimensional data concerning color/Doppler data. For the sake of simplicity, assume that three-dimensional data concerns the B mode. The B-mode data generation unit includes an envelope detector and a logarithmic converter (neither of which is shown). The envelope detector executes envelope detection for the reception signal output from the transmission/reception unit 21. The envelope detector outputs an envelope-detected signal to the logarithmic converter (to be described later). The logarithmic converter relatively enhances a weak signal by logarithmically converting the envelope-detected signal. The B-mode data generation unit generates a signal value (B-mode data) for each depth on each scanning line based on the signal enhanced by the logarithmic converter.

The B-mode data generation unit generates raw data which is B-mode data having a plurality of signal values arranged in the azimuth direction (in which the transducers are arrayed), the elevation direction (the swinging direction of the scan surface), and the depth direction (to be referred to as the range direction hereinafter) in a scanned region. The B-mode data generation unit may execute data interpolation to array data on the line of sight set in advance for rendering processing (to be described later). At this time, the B-mode data generation unit generates line-of-sight data arranged on the line of sight (to be described later) by data interpolation. Note that the B-mode data generation unit may generate volume data (in which voxels are arranged on a gird obtained by dividing a rectangular parallelepiped, which is generally a volume, by a unit length) by converting raw data into raw voxels by data interpolation, or may generate line-of-sight data from raw data or volume data. Note that in this embodiment, raw data, volume data, and line-of-sight data will be generically referred to as three-dimensional data. For the sake of simplicity, the term "three-dimensional data" will be handled as a generic term for these words or will be handled in consideration of raw data without loss of generality. Note that raw data may be data obtained by arranging a plurality of pixel values, a plurality of luminance values, or the like in the azimuth direction, elevation direction, and range direction along scanning lines. The B-mode data generation unit associates three-dimensional data with an absolute coordinate system by using the probe coordinates detected by the position detection unit 10. Note that the B-mode data generation unit may assign coordinates on the absolute coordinate system to three-dimensional data based on probe coordinates. Note that three-dimensional data may be the three-dimensional Doppler data generated by the color/Doppler unit (not shown).

When the operator swings the one-dimensional array probe in a swinging direction, the three-dimensional data generation unit 23 generates three-dimensional data by using B-mode data of each of a plurality of slices respectively corresponding to a plurality of swing angles, and the swing angles and probe positions detected by the position detection unit 10.

The three-dimensional data generation unit 23 may generate combined three-dimensional data by positioning and combining three-dimensional data generated for every movement of the ultrasonic probe 8. The storage unit 31 (to be described later) stores the combined three-dimensional data. The three-dimensional data generation unit 23 executes positioning and combining operation by using the probe position updated for every movement of the ultrasonic probe 8.

The specifying unit 25 specifies a region corresponding to a living body tissue of an object in three-dimensional data by threshold processing. A living body tissue of the object is, for example, a tissue corresponding to the organ name input via the input unit 13 (to be described later). Note that a living body tissue may be a preset tissue or a specific organ. Note that a living body tissue may be decided based on the scan conditions input before ultrasonic scanning. The specifying unit 25 reads out a threshold corresponding to the B-mode data of a set living body tissue or decided living body tissue from the storage unit 31 (to be described later). The specifying unit 25 executes threshold processing by using the threshold read out for each scanning line or line of sight in three-dimensional data. The specifying unit 25 specifies the region of the living body tissue in the three-dimensional data by the above threshold processing. For the sake of simplicity, assume that a living body tissue is a luminal organ. A luminal organ is, for example, a digestive tract, blood vessel, trachea, or the like. At this time, the specifying unit 25 specifies the lumen of a luminal organ as a region of the specific organ. Note that the specifying unit 25 may specify the central line of the lumen instead of the lumen. For the sake of descriptive convenience, assume that the specifying unit 25 specifies the central line of the lumen of the luminal organ. The specifying unit 25 associates the specified central line with the absolute coordinate system by using the probe coordinates decided by the position detection unit 10. Note that the specifying unit 25 may assign coordinates on the absolute coordinate system to the central line based on the probe coordinates.

Note that the specific organ may be an organ such as the uterus or may be read as a tumor, a calculus, or the like developed in the tissue. In addition, the living body tissue may be a fetus in the object.

The setting unit 27 sets a viewpoint used for rendering processing (to be described later) on the central line based on the probe coordinates. The setting unit 27 sets a line of sight with the set viewpoint being a start point on the absolute coordinate system. The line-of-sight direction is, for example, a direction along the central line at the viewpoint (to be referred to as a central line direction hereinafter). Note that the central line direction may be a tangential direction of the central line. The setting unit 27 sets, for example, a predetermined visual angle centered on the line of sight on the absolute coordinate system, with the set viewpoint being a start point. Note that the operator can properly adjust a viewpoint, line of sight, and visual angle via the input unit 13 (to be described later). Note that the setting unit 27 may set a rendering region instead of a visual angle.

More specifically, the setting unit 27 sets a viewpoint setting region in a region occupied by three-dimensional data on the absolute coordinate system. A viewpoint setting region is, for example, a slice of three-dimensional data including the probe coordinates. The setting unit 27 decides the intersection point between the viewpoint setting region and the central line as a viewpoint. Note that the setting unit 27 decides, as a viewpoint, the intersection point between the central line and a straight line extending from the probe coordinates in the scanning line direction. In addition, the setting unit 27 may set a viewpoint at the position of the central line immediately below the probe coordinates. Note that the setting unit 27 may set the intersection region between the viewpoint setting region and the lumen as a viewpoint.

When the operator moves the ultrasonic probe 8 while keeping it in contact with the body surface of the object, the setting unit 27 moves the viewpoint along the central line at a velocity and in a direction respectively corresponding to the moving velocity (to be referred to as a probe velocity hereinafter) and moving direction of the ultrasonic probe 8. More specifically, the setting unit 27 sets viewpoints at preset time intervals, predetermined position intervals, or continuously at the same velocity as the probe velocity. Note that the setting unit 27 may move the viewpoint along the central line at a predetermined constant velocity stored in the storage unit 31 (to be described later) or the constant velocity set by the input unit 13 (to be described later). At this time, the setting unit 27 may change the moving velocity of the viewpoint to the moving velocity of the ultrasonic probe 8 when the viewpoint is moved to a predetermined region in the generated three-dimensional data.

Note that the setting unit 27 may reversely set the moving direction of the above viewpoint, the start and end points of the movement of the viewpoint, and the line of sight on the central line specified in combined three-dimensional data. This reverse setting operation reverses the display order of the perspective projection images (or parallel projection images) generated by the image generation unit 29. That is, the display unit 12 displays the perspective projection image in the reverse line-of-sight direction to the perspective projection image displayed accompanying the movement of the ultrasonic probe 8, with the start and end points of the movement of the viewpoint being reversed.

The image generation unit 29 executes rendering processing by using the viewpoint set by the setting unit 27 and the three-dimensional data. Rendering processing is, for example, surface rendering or volume rendering. More specifically, the image generation unit 29 executes perspective projection of the three-dimensional data as rendering processing by using the viewpoint, line of sight, and visual angle. For the sake of simplicity, assume that rendering processing executed by perspective projection is surface rendering. Note that the image generation unit 29 may execute parallel projection of the three-dimensional data as rendering processing by using the viewpoint, line of sight, and rendering region. For the sake of simplicity, rendering processing executed in parallel projection is volume rendering. Note that volume rendering may be, for example, MIP (Maximum Intensity Projection). The image generation unit 29 executes perspective projection or parallel projection at predetermined time intervals, predetermined position intervals, or continuously by using the viewpoints set at predetermined intervals or continuously and the line of sight.

The image generation unit 29 generates an ultrasonic image by perspective projection (to be referred to as a perspective projection image hereinafter). The image generation unit 29 generates an ultrasonic image by parallel projection (to be referred to as a parallel projection image hereinafter). The image generation unit 29 sequentially generates perspective projection images accompanying the movement of the viewpoint. The image generation unit 29 may generate an MPR (Multi-Planar Reconstruction) image by using three-dimensional data. The image generation unit 29 may generate the first combination image by combining the MPR image and the perspective projection image which are juxtaposed to each other. The image generation unit 29 may generate the second combination image by combining the MPR image and the parallel projection image which are juxtaposed to each other. The image generation unit 29 converts a signal string in the generated ultrasonic image into a signal string in a general video format typified by a TV format or the like, and generates an ultrasonic image as a display image. Note that the image generation unit 29 may generate a color/Doppler image based on the color/Doppler signal output from a color/Doppler processing unit (not shown). The image generation unit 29 may generate a general B-mode image concerning a slice of a scanned region.

Note that the image generation unit 29 may generate a perspective projection image along the reversed moving direction of the viewpoint by using the reversed start point, end point, and line of sight on the central line specified in combined three-dimensional data.

The storage unit 31 stores a plurality of reception delay patterns with different focus depths, control programs for the ultrasonic diagnostic apparatus 1, a diagnostic protocol, various kinds of data such as transmission/reception conditions, three-dimensional data, combined three-dimensional data, Doppler data, the perspective projection images, parallel projection images and MPR images generated by the image generation unit 29, and a program concerning an algorithm for deciding a threshold, reference position, and viewpoint for specifying a living body tissue. The storage unit 31 stores an ultrasonic image, line-of-sight data, and the like immediately before freeze operation performed via the input unit 13 (to be described later). The storage unit 31 stores a threshold for specifying a luminal organ which is used by the specifying unit 25. Note that the storage unit 31 may store a predetermined constant velocity concerning the movement of a viewpoint which is used by the setting unit 27.

The CPU 33 reads out transmission/reception conditions and an apparatus control program stored in the storage unit 31 based on mode selection, selection of a reception delay pattern list, and transmission start/end input by the operator via the input unit 13, and controls the apparatus main body 11 in accordance with these pieces of information. For example, the CPU 33 controls the specifying unit 25, the setting unit 27, and the image generation unit 29 in accordance with control programs read out from the storage unit 31.

The I/F 35 is an interface concerning the input unit 13, a network, an external storage device (not shown), and a biological signal measurement unit (not shown). Data such as ultrasonic images, analysis results, and the like obtained by the apparatus main body 11 can be transferred to other apparatuses via the I/F 35 and the network.

The display unit 12 includes a monitor (not shown). The display unit 12 displays various kinds of images generated by the image generation unit 29 on the monitor. More specifically, for example, the display unit 12 consecutively displays the perspective projection images generated accompanying the movement of the viewpoint on the monitor. Note that the display unit 12 may display an MPR image corresponding to a perspective projection image and a parallel projection image. In addition, the display unit 12 may execute adjustment concerning brightness, contrast, dynamic range, γ correction, and the like and color mapping for the ultrasonic images and MPR images generated by the image generation unit 29. Note that the display unit 12 may switchably display the first and second combination images generated by the image generation unit 29.

Note that the display unit 12 can also display the perspective projection image generated by the image generation unit 29 upon reversal of the moving direction of the viewpoint.

The input unit 13 is connected to the I/F 35 and inputs various kinds of instructions, commands, information, selections, and settings from the operator to the apparatus main body 11. The input unit 13 includes input devices such as a trackball, switch buttons, mouse, and keyboard (not shown). The input device detects the coordinates of a cursor displayed on the display screen, and outputs the detected coordinates to the CPU 33. Note that the input device may be a touch panel provided to cover the display screen. In this case, the input unit 13 detects a touched and designated coordinates by a coordinate reading principle such as an electromagnetic induction scheme, magnetostriction scheme, or a pressure-sensitive scheme, and outputs the detected coordinates to the CPU 33. When, for example, the operator operates the end button or freeze button of the input device 13, the transmission/reception of ultrasonic waves is terminated, and the apparatus main body 11 is set in a pause state.

Note that the input unit 13 may input a region corresponding to the living body tissue specified by the specifying unit 25 or the central line of the lumen of a luminal organ in accordance with an instruction from the operator. The input unit 13 may input the viewpoint, line of sight, and visual angle set by the setting unit 27 in accordance with an instruction from the operator. Note that the input unit 13 may input a threshold to be used by the specifying unit 25. The input unit 13 inputs an instruction to switch display between the first and second combination images. Note that the input unit 13 may input a constant velocity of a viewpoint in accordance with an instruction from the operator.

The input unit 13 also includes a button or the like which inputs the reversal of the moving direction of a viewpoint. When the operator operates this button, the apparatus generates and displays a perspective projection image along the reversed moving direction of the viewpoint by using the reversed start point, end point, and line of sight and combined three-dimensional data along the central line specified in the combined three-dimensional data.

(Perspective Projection Image Generation Function)

The perspective projection image generation function is a function of deciding a viewpoint and a line of sight based on the probe coordinates decided by the position detection unit 10, and generating a perspective projection image based on the decided viewpoint and line of sight. Processing concerning the perspective projection image function (to be referred to as perspective projection image generation processing hereinafter) will be described below.

FIG. 2 is a flowchart showing a procedure for the processing of generating a perspective projection image.

Before ultrasonic transmission/reception with respect to an object, the apparatus executes input of patient information, setting and updating of transmission/reception conditions and various kinds of ultrasonic data acquisition conditions, and the like in accordance with instructions from the operator via the input unit 13. The storage unit 31 stores these settings and updates. Upon completion of these inputting/selecting/setting/deciding operations, the operator brings the ultrasonic probe 8 into contact with the body surface of the object at a predetermined position (step Sa1).

Probe coordinates are detected with reference to a predetermined reference position (step Sa2). The transmission/reception unit 21 then transmits ultrasonic waves to the object. A reception signal is generated based on the reception of an echo signal (i.e., ultrasonic scanning) corresponding to the transmitted ultrasonic waves (step Sa3). The apparatus generates three-dimensional data based on the reception signal (step Sa4). At this time, the apparatus assigns the generated three-dimensional data with coordinates on the absolute coordinate system (to be referred to as absolute coordinates hereinafter) based on the probe coordinates. The apparatus specifies the central line of the lumen in the generated three-dimensional data by threshold processing (step Sa5). Absolute coordinates are assigned to the specified central line. The apparatus sets a viewpoint on the central line on the absolute coordinate system based on the probe coordinates and the predetermined reference position. In addition, a line of sight and a visual angle are set, with the set viewpoint being a start point (step Sa6). At this time, the position of the viewpoint, the direction of the line of sight, and the visual angle are set on the absolute coordinate system. The apparatus generates a perspective projection image by using the set viewpoint and line of sight based on the three-dimensional data (step Sa7). The apparatus executes the above processing in accordance with the movement of the ultrasonic probe 8 (step Sa8). At this time, the position detection unit 10 updates the probe position information.

Figure 3:
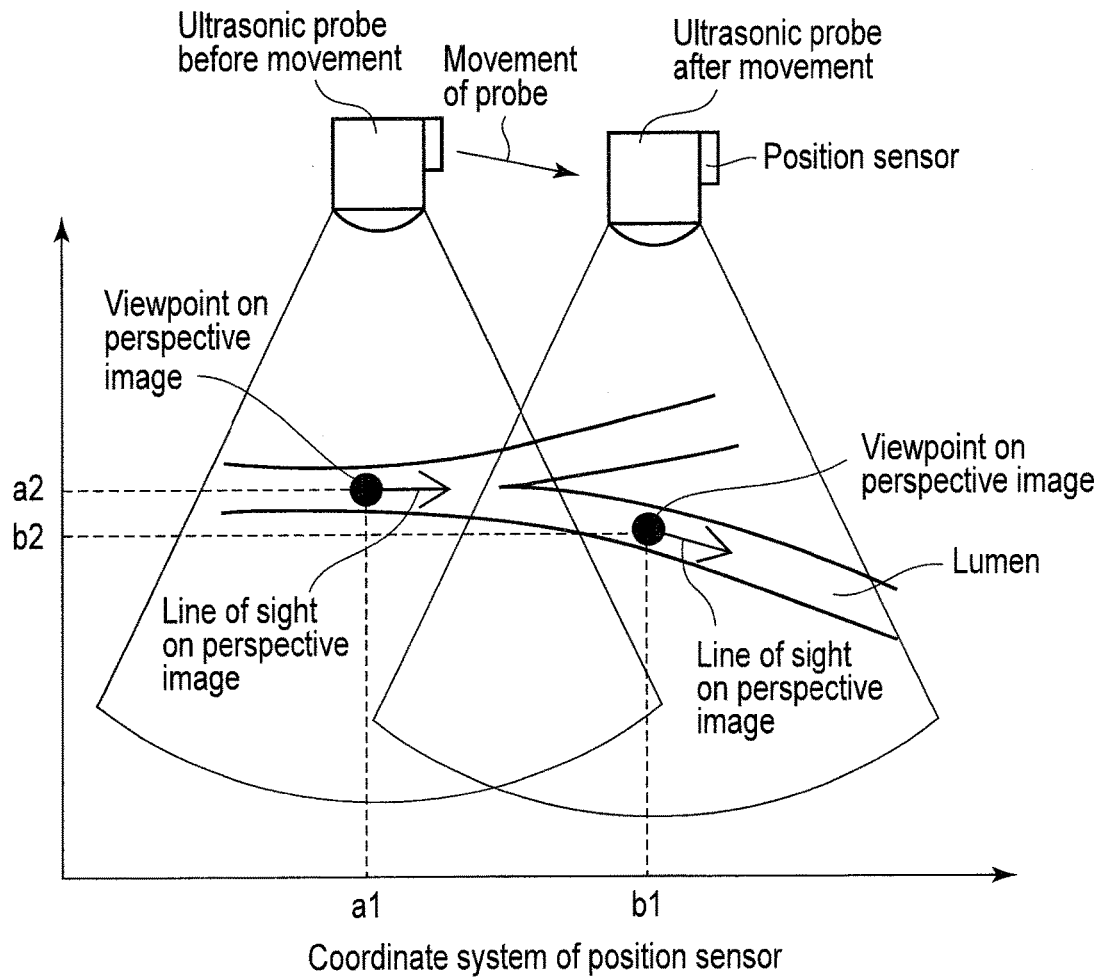
FIG. 3 is a view showing an example according to this embodiment in which after an ultrasonic probe is moved, a viewpoint and a line of sight are set in the lumen in three-dimensional data obtained next.

FIG. 3 is a view showing an example of setting a viewpoint and a line of sight in the lumen in the three-dimensional data obtained next after the movement of the ultrasonic probe 8. For the sake of simplicity, FIG. 3 shows the coordinate system (absolute coordinate system) of the position sensor 9 as a two-dimensional coordinate system. Probe coordinates concerning the ultrasonic probe 8 before movement are (a1, a2). Probe coordinates concerning the ultrasonic probe 8 after movement are (b1, b2). The apparatus generates a perspective projection image by using the viewpoint and line of sight set with the probe coordinates.

Figure 4:
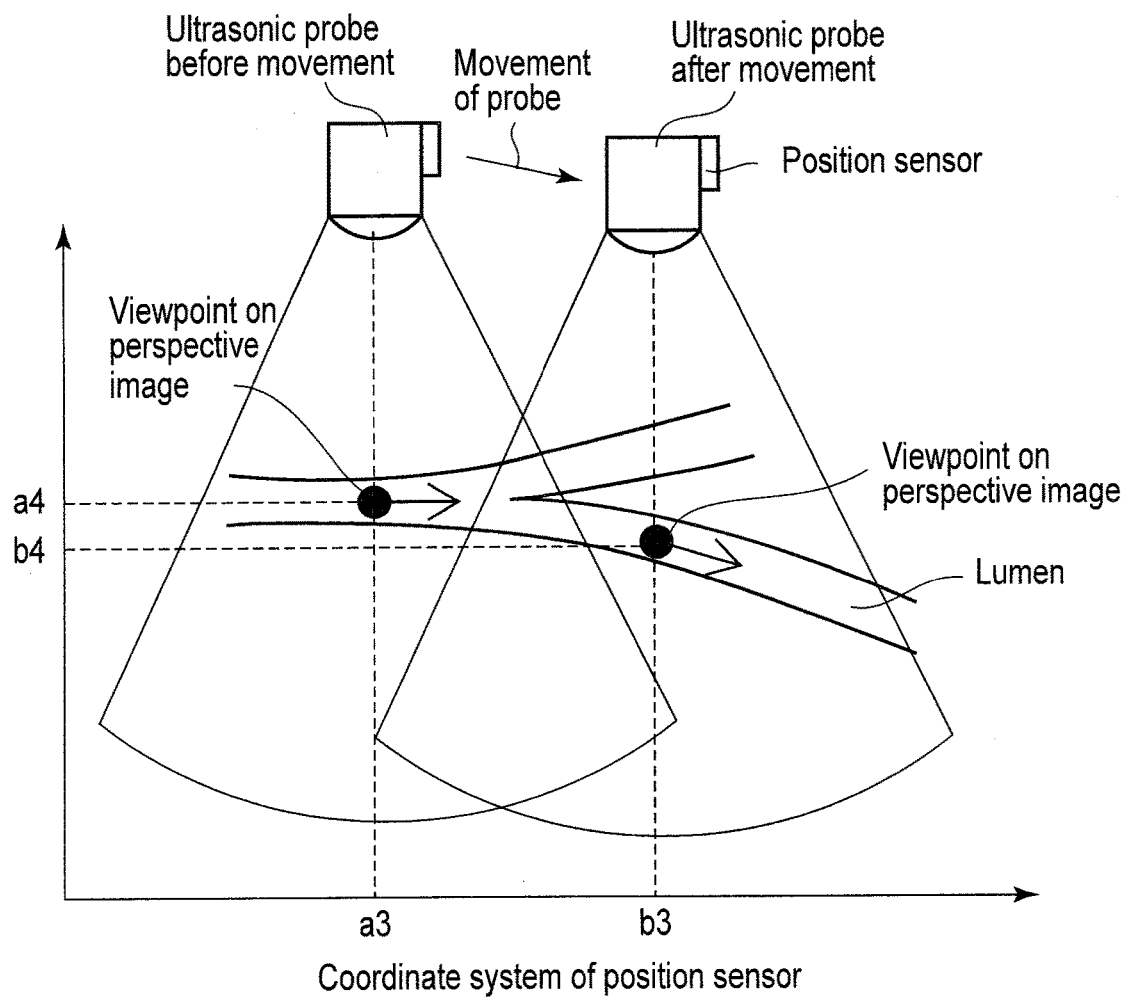
FIG. 4 is a view showing an example according to this embodiment in which after the ultrasonic probe is moved, a viewpoint is set in the lumen immediately below the ultrasonic probe.

FIG. 4 is a view showing an example of setting a viewpoint and in the lumen immediately below the ultrasonic probe 8 after the movement of the ultrasonic probe 8. FIG. 4 differs from FIG. 3 in that each viewpoint is set immediately below the ultrasonic probe 8.

Figure 5:
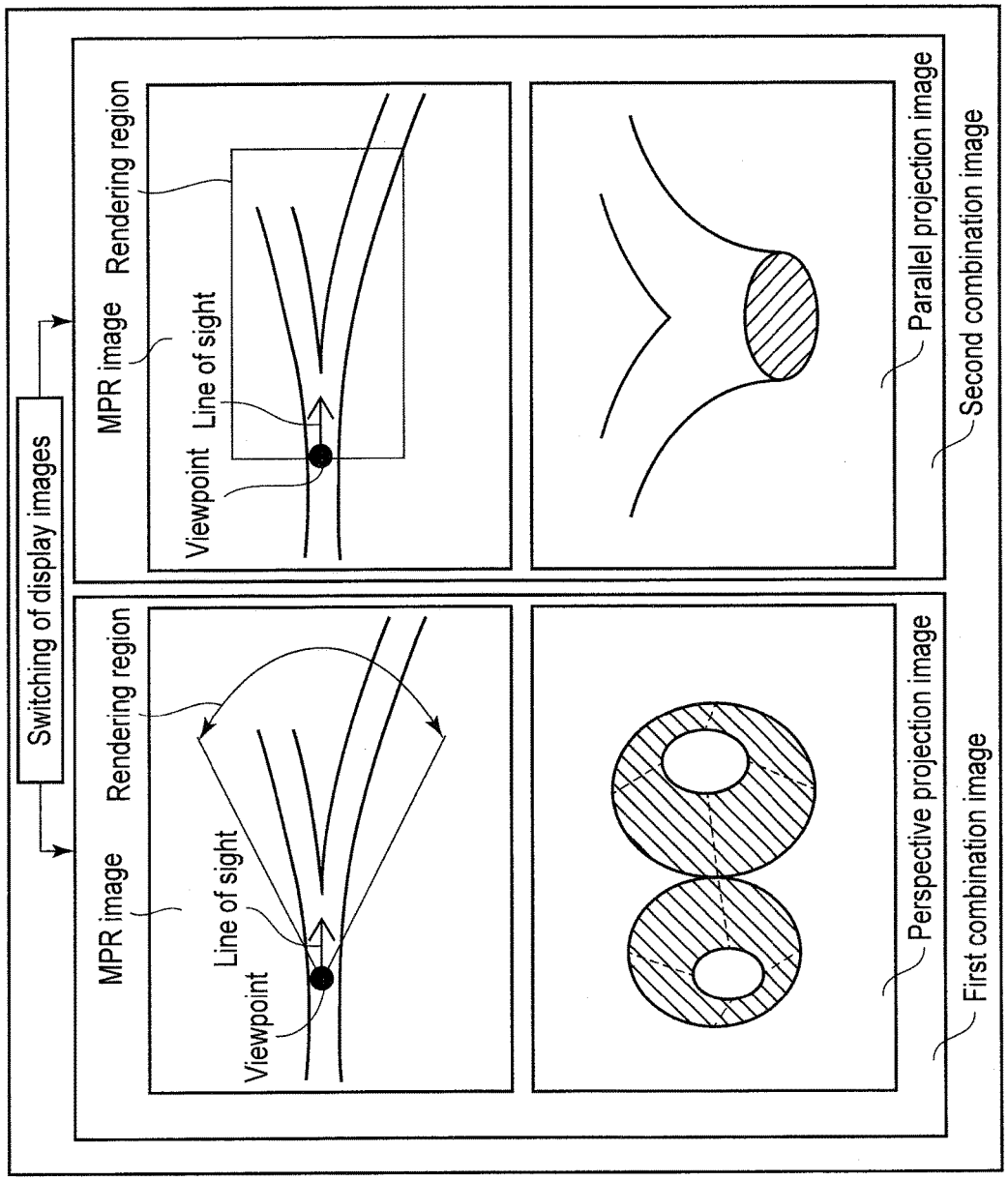
FIG. 5 is a view showing an example of the first and second combination images, according to this embodiment, which can be switched and displayed by a display unit.

FIG. 5 is a view showing an example of the first and second combination images which can be switched and displayed by the display unit 12. The first combination image includes a perspective projection image and an MPR image indicating a viewpoint, line of sight, and visual angle. The second combination image includes a parallel projection image and an MPR image indicating a viewpoint, line of sight, and visual angle. The apparatus properly switches the first and second combination images in accordance with the instruction input by the operator via the input unit 13.

First Modification

The first modification differs from the above embodiment in that after the ultrasonic probe 8 is moved, the coordinates of the viewpoint on the absolute coordinate system are maintained at the coordinates of the viewpoint set based on the probe coordinates concerning the ultrasonic probe 8 before the movement. In addition, the three-dimensional data generated after the movement of the ultrasonic probe 8 (to be referred to as after-movement three-dimensional data hereinafter) can be combined with the three-dimensional data generated before the movement of the ultrasonic probe 8 (to be referred to as before-movement three-dimensional data hereinafter).

The setting unit 27 maintains the viewpoint after the movement of the ultrasonic probe 8 at the coordinates of the viewpoint set based on the probe coordinates concerning the ultrasonic probe 8 before the movement.

The three-dimensional data generation unit 23 combines the before-movement three-dimensional data with the after-movement three-dimensional data based on the coordinates of the absolute coordinate system. The three-dimensional data generation unit 23 generates combined three-dimensional data by combining these three-dimensional data on the absolute coordinate system. Note that even if the before-movement three-dimensional data and the after-movement three-dimensional data are spaced apart from each other on the absolute coordinate system by a distance that does not allow them to be combined, the three-dimensional data generation unit 23 may define the three-dimensional data before and after the movement on the absolute coordinate system.

The image generation unit 29 may generate rendering image by rendering processing by using the maintained viewpoint and the three-dimensional data generated before and after the movement of the ultrasonic probe 8. When, for example, the operator moves the ultrasonic probe 8 away from the point at which the viewpoint is maintained, a rendering image is displayed at a position far from the viewpoint. The image generation unit 29 may also generate a rendering image by rendering processing using the maintained viewpoint and combined three-dimensional data. A living body tissue is not limited to a luminal organ, and may be the uterus or a fetus in the object. If a living body tissue is the uterus or a fetus in the object, the viewpoint to be maintained is located in the uterus or amniotic fluid.

Figure 6:
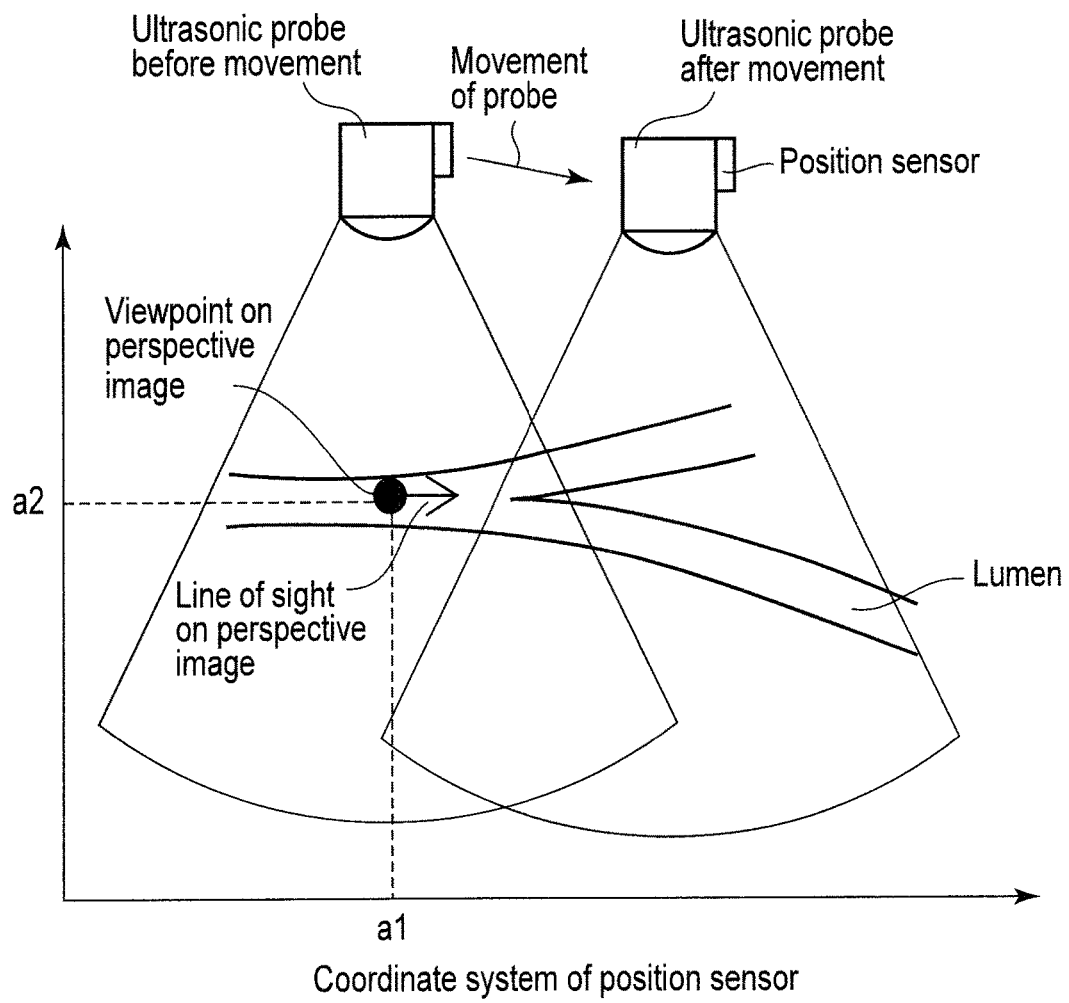
FIG. 6 is a view showing an example according to the first modification of this embodiment in which after the ultrasonic probe is moved, a viewpoint and a line of sight are maintained in the lumen in the three-dimensional data obtained before the movement of the ultrasonic probe.

FIG. 6 is a view showing an example of maintaining a viewpoint and a line of sight in the lumen in before-movement three-dimensional data after the movement of the ultrasonic probe. Referring to FIG. 6, the after-movement three-dimensional data may be combined with the before-movement three-dimensional data. In this case, the display unit 12 displays a perspective projection image at the probe coordinates concerning the ultrasonic probe 8 before the movement. Subsequently, for example, the setting unit 27 sets a viewpoint on a central line in accordance with an instruction to continuously display a perspective projection image which, is issued via the input unit 13. The image generation unit 29 executes rendering processing by using the set viewpoint and before-movement three-dimensional data. The display unit 12 displays the perspective projection image or the like having undergone the rendering processing on the monitor.

Second Modification

The second modification differs from the first modification in that it controls the transmission of ultrasonic waves in response to the movement of the viewpoint to a predetermined region near an end portion of three-dimensional data (to be referred to as an end portion region hereinafter).

The setting unit 27 sets an end portion region near an end portion of three-dimensional data. More specifically, the setting unit 27 sets a region having a width corresponding to the distance obtained by multiplying the sum of the time required for ultrasonic scanning and the time taken to generate a perspective projection image by the moving velocity of the viewpoint as an end portion region at an end portion of the three-dimensional data. Note that it is possible to properly adjust an end portion region in accordance with an instruction from the operator via the input unit 13. In addition, the storage unit 31 may store an end portion region in advance.

The CPU 33 controls the transmission/reception unit 21 to supply a driving signal to each ultrasonic transducer in response to when the viewpoint reaches the end portion region. Note that the CPU 33 may control the transmission/reception unit 21 not to supply any driving signal to each ultrasonic transducer if the tangential direction of the central line at the position of the viewpoint which has reached the end portion region is parallel to the scanning line direction. In this case, the CPU 33 may also control the display unit 12 to display an error.

Note that the CPU 33 may change ultrasonic transmission conditions such as a depth of field, the number of scanning lines, transmission center frequency, and focus depth based on the position of a viewpoint in an end portion region. For example, the CPU 33 changes ultrasonic transmission conditions in accordance with the ratio of the depth of the viewpoint in an end portion region to the depth of field in a scanned region. If, for example, the ratio is 80% or more, the CPU 33 controls the transmission/reception unit 21 to increase the depth of field by 1.5 times. Note that the CPU 33 can also change the transmission center frequency in accordance with the depth of field. In addition, the CPU 33 may properly change the focus depth based on the depth of the viewpoint in the end portion region and the line-of-sight direction at the viewpoint in the end portion region.

Figure 7:
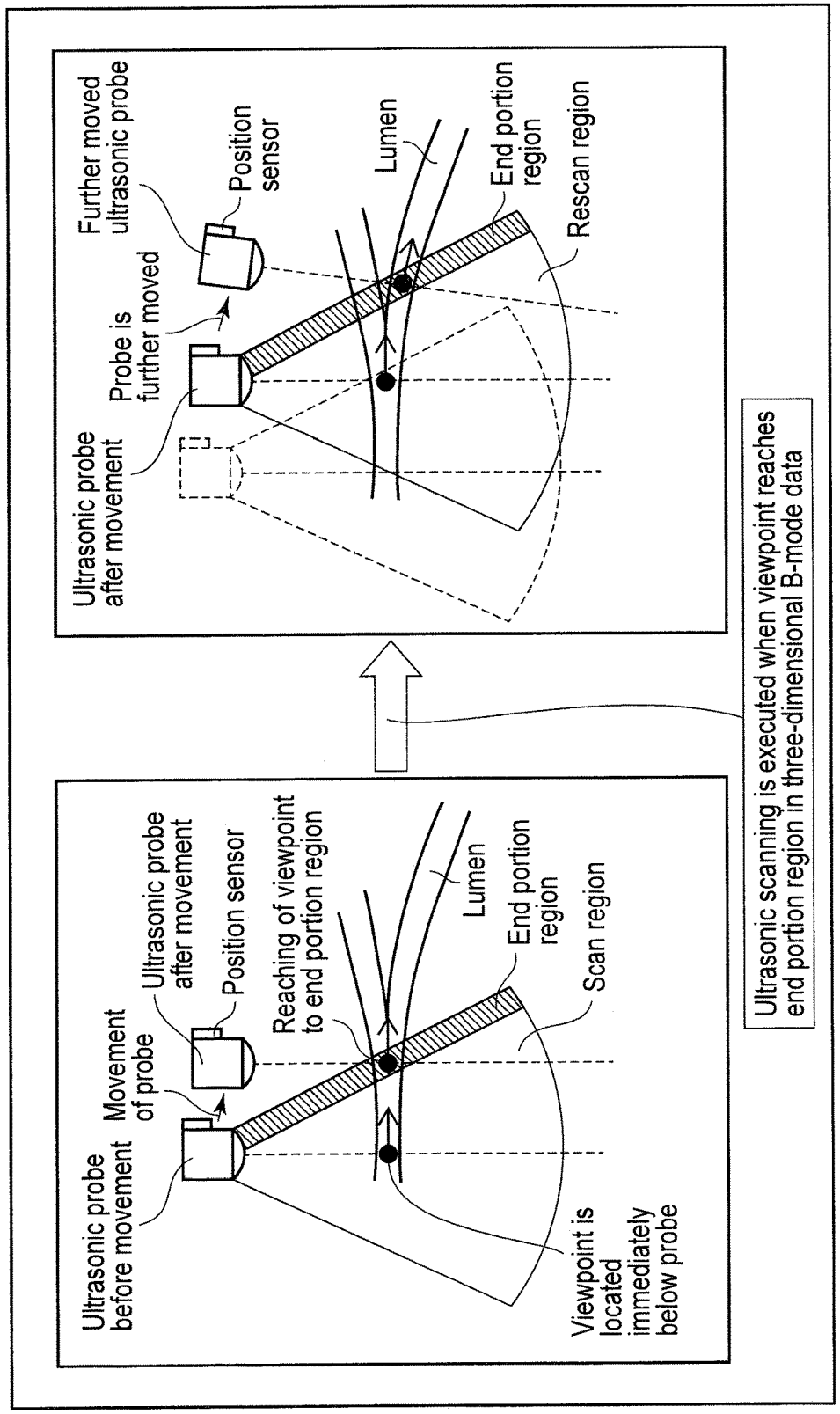
FIG. 7 is a view showing an example according to the second modification of this embodiment in which when the viewpoint reaches an end portion region in three-dimensional data, ultrasonic scanning is executed.

FIG. 7 is a view showing an example of executing ultrasonic scanning when a viewpoint reaches an end portion region. Referring to FIG. 7, a viewpoint is set on a central line immediately below the ultrasonic probe 8. The viewpoint moves accompanying the movement of the ultrasonic probe 8. When the moved viewpoint reaches the preset end portion region, the apparatus executes ultrasonic scanning.

Figure 8:
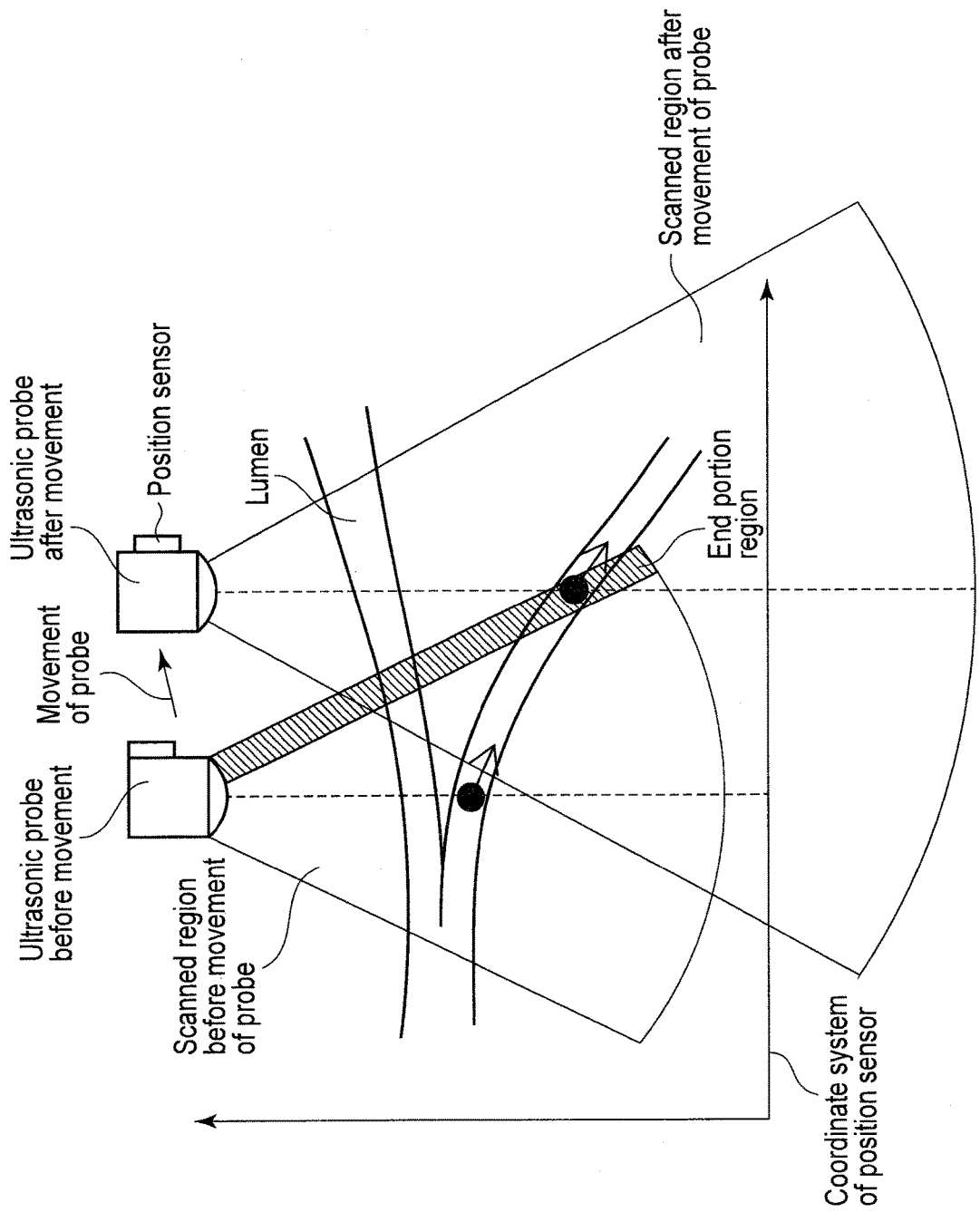
FIG. 8 is an example according to the second modification of this embodiment in which the depth of field in a scanned region is changed based on the position of the viewpoint when it has reached an end portion region of three-dimensional data.

FIG. 8 is a view showing an example of changing the depth of field in a scanned region based on the position of the viewpoint when the viewpoint has reached an end portion region of three-dimensional data. A depth of field in a scanned region concerning ultrasonic scanning after the movement of the ultrasonic probe 8 is decides in accordance with the ratio of the depth of the viewpoint in an end portion region to the depth of field in the scanned region concerning ultrasonic scanning before the movement of the ultrasonic probe 8. The apparatus executes ultrasonic scanning after the movement of the ultrasonic probe 8 at the decided depth of field. As processing after ultrasonic scanning, a line of sight is set on the central line, and a perspective projection image or the like is displayed on the monitor.

Third Modification

The third modification differs from the first and second modifications in that if the lumen branches, one lumen is displayed depending on the movement of the ultrasonic probe 8.

The position sensor 9 acquires probe position information with reference to a predetermined reference position. The probe position information includes the position of the ultrasonic probe 8 relative to the predetermined reference position and the angle of the ultrasonic probe 8. The angle of the ultrasonic probe 8 is, for example, the inclination of the ultrasonic probe 8 relative to a predetermined reference direction. The predetermined reference position is, for example, the position of the apparatus main body 11 of the ultrasonic diagnostic apparatus 1. The predetermined reference direction is defined by, for example, preset three orthogonal axes. The position sensor 9 is provided on, for example, the ultrasonic probe 8. The position sensor 9 outputs the acquired probe position information to the position detection unit 10 (to be described later).

The position sensor 9 is, for example, a magnetic sensor, infrared sensor, angle sensor, or angular velocity sensor (e.g., a gyro sensor). For example, the magnetic sensor acquires probe position information with reference to a predetermined reference position by using the magnetism transmitted from a magnetic transmitter (not shown) in the position detection unit 10 (to be described later). The infrared sensor acquires probe position information with reference to the predetermined reference position by using the infrared rays transmitted from an infrared transmitter (not shown) in the position detection unit 10 (to be described later). Note that more commonly used electromagnetic waves may be used instead of infrared rays. Note that if the position sensor 9 is a magnetic sensor, a reference position may be the position of the magnetic transmitter. In addition, if the position sensor 9 is an infrared sensor, a reference position may be the position of the infrared transmitter. It is possible to properly adjust a reference position in accordance with an instruction from the operator via the input unit 13 (to be described later). Note that a predetermined reference position may be a position at which the probe comes into contact with the body surface of the object for the first time.

The angle sensor detects the angle of the ultrasonic probe 8 relative to the body surface of an object. The angular velocity sensor detects an angular velocity corresponding to the movement of the ultrasonic probe 8. An output from an angle sensor or an acceleration sensor in the position sensor 9 is called angle information. Note that angle information may be decided based on the positions of two points output from two magnetic sensors, two infrared sensors, or a combination of a magnetic sensor and an infrared sensor provided on a side surface of the ultrasonic probe 8.

The position detection unit 10 decides the moving direction of the ultrasonic probe 8 based on probe position information. The moving direction is defined by, for example, a unit vector on an absolute coordinate system (to be referred to as a probe direction vector hereinafter). The position detection unit 10 decides probe direction vectors at predetermined intervals accompanying the movement of the ultrasonic probe 8.

The specifying unit 25 decides a unit vector of the central line on the absolute coordinate system (to be referred to as a central line direction vector hereinafter) for each viewpoint position. For the sake of simplicity, assume that the lumen branches into two directions at a branching portion. The central line branches into the first and second central lines at the branching portion of the lumen. The specifying unit 25 decides the first central line direction vector concerning the first central line and the central line direction vector concerning the second central line at the branching portion.

The setting unit 27 sets a viewpoint on the central line of one of the branching lumens with reference to a predetermined reference position based on a probe direction vector and a central line direction vector. More specifically, the setting unit 27 calculates the inner product (to be referred to as the first inner product hereinafter) of the probe direction vector and the first central line direction vector located immediately below the probe direction vector. The first inner product corresponds to the cosine of the angle between the probe direction vector and the first central line direction vector. The setting unit 27 calculates the inner product (to be referred to as the second inner product hereinafter) of the probe direction vector and the second central line direction vector located immediately below the probe direction vector.

The second inner product corresponds to the cosine of the angle between the probe direction vector and the second central line direction vector. Note that the first and second central line direction vectors are located in the same plane (for example, a scanning surface). At least one of the azimuth direction and elevation direction on this plane differs.

The setting unit 27 specifies a central line direction vector concerning a larger one of the calculated first and second inner products. The setting unit 27 sets a viewpoint on a central line concerning the specified central line direction vector. Note that the setting unit 27 may specify a central line direction vector concerning a larger one of the absolute values of the first and second inner products. At this time, it is possible to reverse the line of sight (the moving direction of the viewpoint). To reverse the moving direction of a viewpoint is equivalent to make the inner product negative. Note that when the lumen branches perpendicularly, the setting unit 27 may set a viewpoint based on the focus position input via the input unit 13.

The image generation unit 29 executes rendering processing by using the set viewpoint and three-dimensional data. The display unit 12 displays the perspective projection image having undergone rendering processing.

Figure 9:
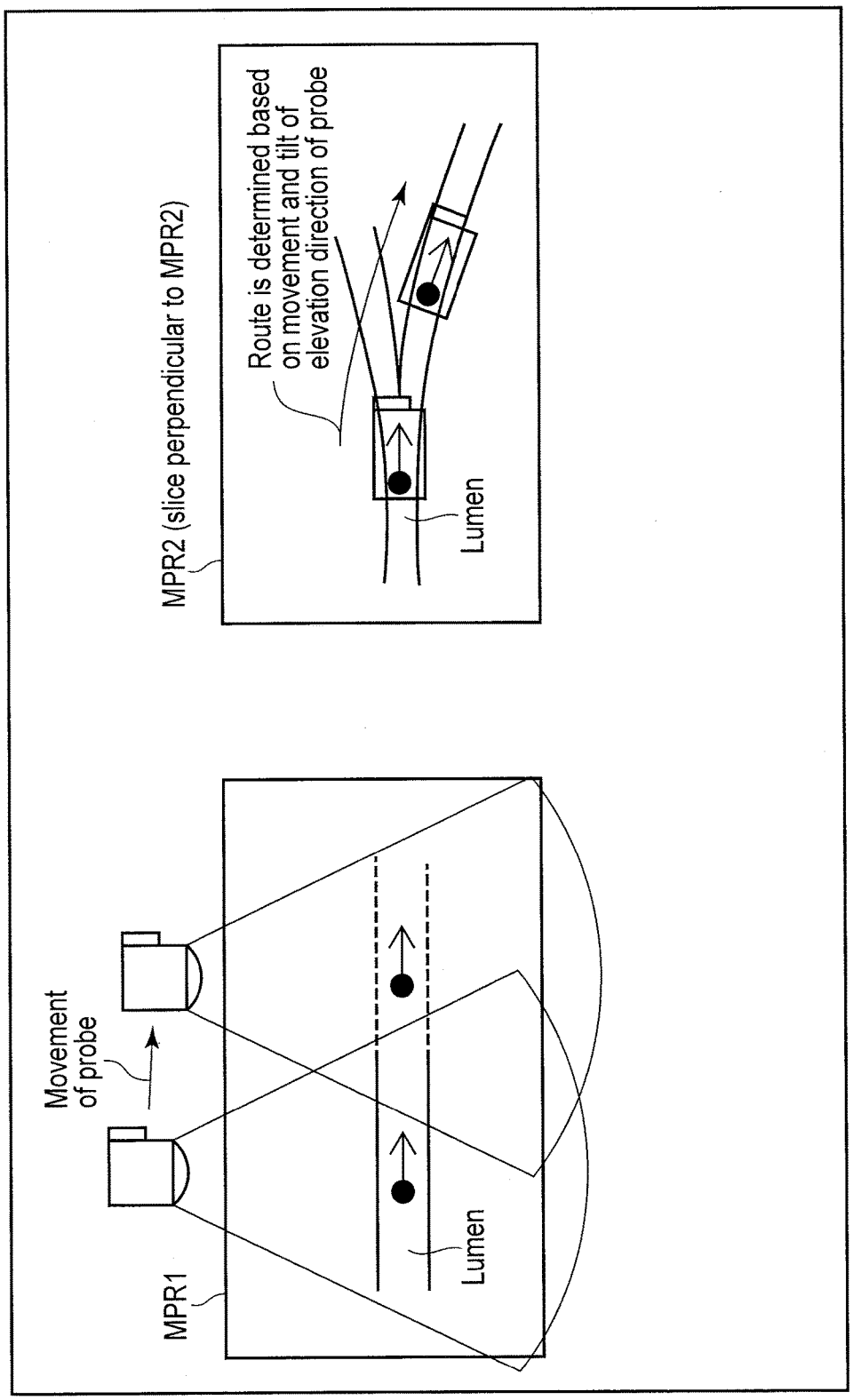
FIG. 9 is a view showing an example according to the third modification of this embodiment in which a lumen near immediately below an ultrasonic probe is selected and the viewpoint is moved, at a branching point of a lumen, in accordance with the angle and moving direction of the ultrasonic probe.

FIG. 9 is a view showing an example of selecting a lumen near immediately below the ultrasonic probe in accordance with the angle and moving direction of the ultrasonic probe, at a branching point of the lumen, and moving the viewpoint. In the MPR1 image, the lumen indicated by the dotted lines falls (branches) outside a slice of MPR1. In the MPR2 image (a slice perpendicular to MPR1), the path of the lumen is specified based on the movement and tilt of elevation direction (angle information) of the probe.

Fourth Modification

The fourth differs from the first to third modifications in that when the lumen bends, the direction in which the ultrasonic probe 8 is to be guided is displayed to execute ultrasonic scanning on the lumen to be displayed.

The setting unit 27 sets a lumen peripheral region having a predetermined thickness around the lumen specified by the specifying unit 25. Note that it is possible to properly adjust the lumen peripheral region in accordance with an instruction from the operator via the input unit 13.

The position detection unit decides the moving direction of the ultrasonic probe accompanying the movement of the ultrasonic probe 8.

The specifying unit 25 specifies the tangential direction of a central line at a viewpoint. The specifying unit 25 specifies a plane perpendicular to the moving direction of the ultrasonic probe 8 (to be referred to as a perpendicular plane hereinafter). A perpendicular plane is, for example, an ultrasonic scanning plane. The specifying unit 25 determines whether a perpendicular plane includes a lumen peripheral region. If the lumen peripheral region falls outside the perpendicular plane accompanying the movement of the ultrasonic probe 8, the specifying unit 25 outputs the tangential direction at this time to the display unit 12.

The display unit 12 displays the position of the ultrasonic probe 8 on a body mark. The display unit 12 superimposes and displays the tangential direction output from the specifying unit 25 on the body mark on which the position of the ultrasonic probe 8 is displayed.

Figure 10:
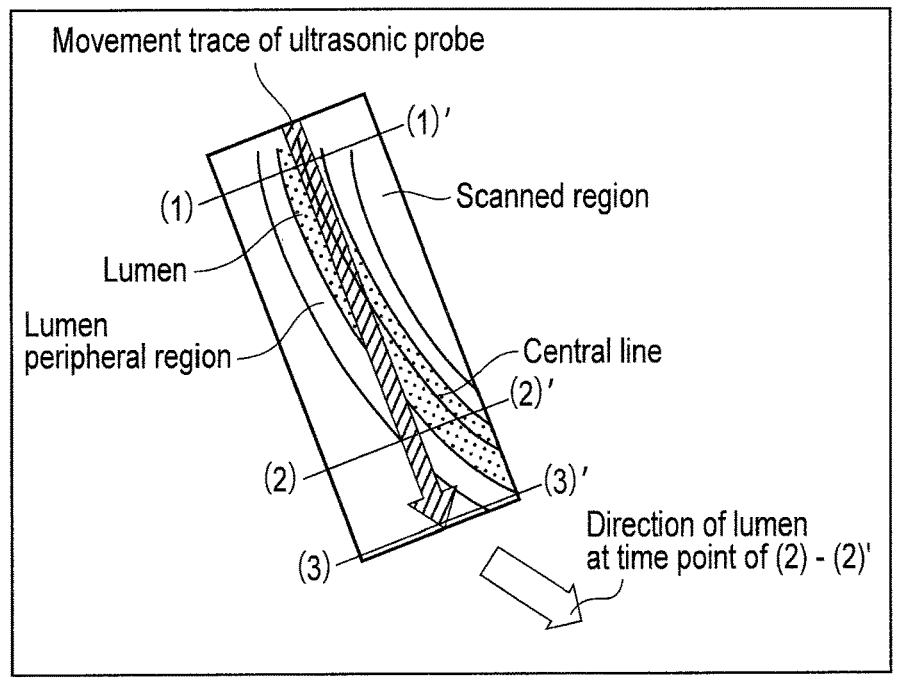
FIG. 10 is a view showing a parallel projection view obtained by parallel projection of a scanned region, lumen peripheral region, lumen, and central line from the back surface direction of the ultrasonic probe, together with the movement trace of the ultrasonic probe, according to the fourth modification of this embodiment.

FIG. 10 is a view showing a parallel projection view obtained by parallel projection of a scanned region, lumen peripheral region, lumen, and central line from the back surface direction of the ultrasonic probe, together with the movement trace of the ultrasonic probe 8. As shown in FIG. 10, the specifying unit 25 determines that a lumen peripheral region falls outside a perpendicular plane (2)-(2)'. The specifying unit 25 outputs the direction of the lumen on the perpendicular plane (2)-(2)' to the display unit 12.

Figure 11:
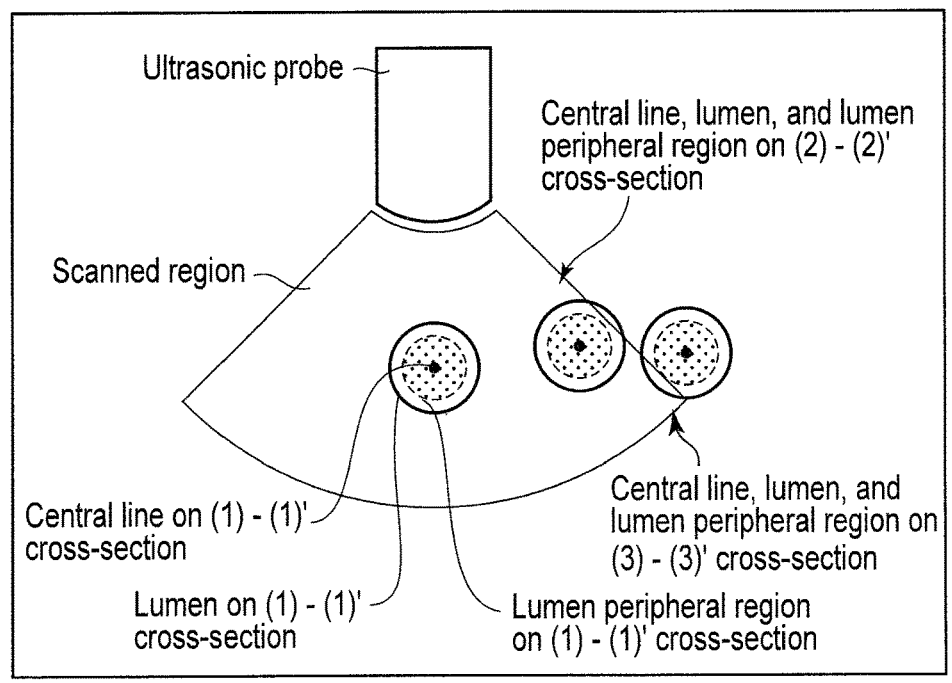
FIG. 11 is view showing a central line, lumen, and lumen peripheral region in each of a (1)-(1)' cross-section, (2)-(2)' cross-section, and (3)-(3)' cross-section in FIG. 10, together with a scanned region, according to the fourth modification of this embodiment.

FIG. 11 is a view showing a central line, lumen, and lumen peripheral region in each of a (1)-(1)' cross-section, (2)-(2)' cross-section, and (3)-(3)' cross-section in FIG. 10, together with a perpendicular plane in a scanned region. FIG. 11 shows an example in which a lumen peripheral region has fallen outside the perpendicular plane (2)-(2)'.

Figure 12:
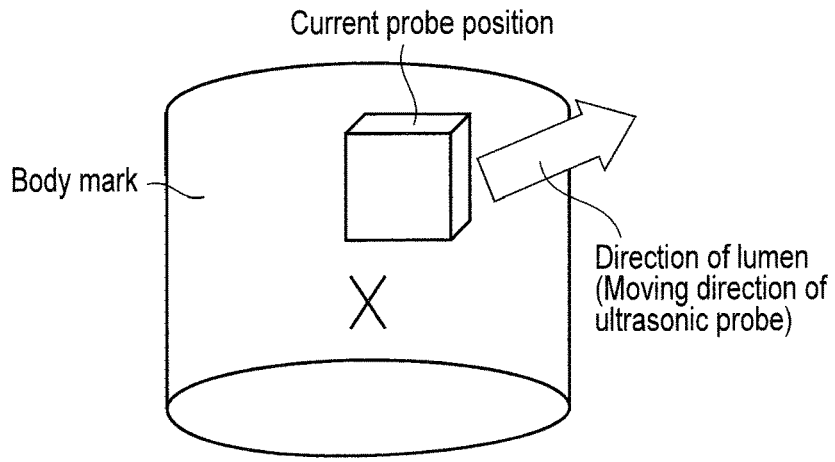
FIG. 12 is a view showing the ultrasonic probe and a lumen direction in a three-dimensional body mark according to the fourth modification of this embodiment.
Figure 13:
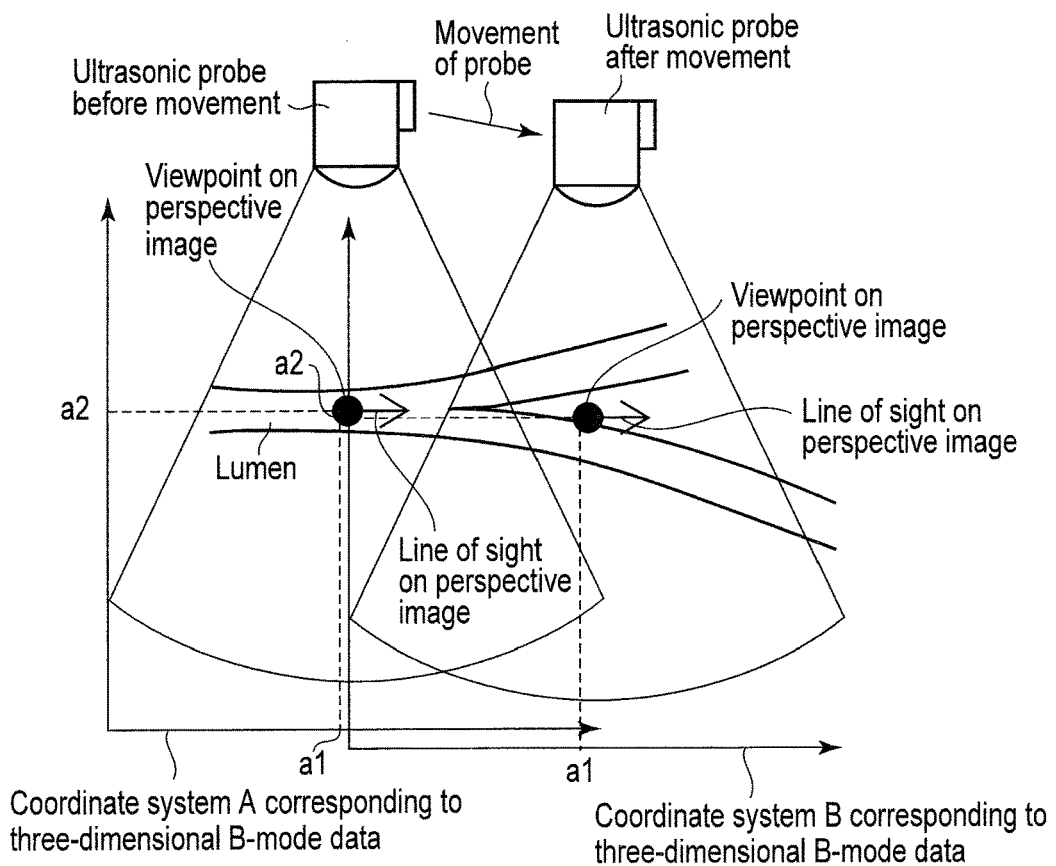
FIG. 13 is a view showing how the position of a viewpoint set in advance for each three-dimensional data falls outside the interior of a lumen in the three-dimensional data obtained after the movement of the probe according to the prior art.

FIG. 12 is a view showing the ultrasonic probe 8 and the direction of the lumen on a body mark. The direction of the lumen output from the specifying unit 25 is superimposed and displayed on the body mark.

According to the above arrangement, the following effects can be obtained.

According to the ultrasonic diagnostic apparatus 1, it is possible to set a viewpoint in a living body tissue region specified in three-dimensional data based on the position of the ultrasonic probe 8 detected as a predetermined reference position. This makes it possible to maintain a viewpoint in the living body tissue and generate a rendering image at the viewpoint in the living body tissue even when the ultrasonic probe 8 is moved. For example, the viewpoint set immediately below the ultrasonic probe 8 can be maintained in the lumen even when ultrasonic scanning is executed again. Note that it is also possible to make the moving velocity of a viewpoint concerning a rendering image differ from that of the ultrasonic probe 8. In this case, when the viewpoint reaches a predetermined region in three-dimensional data, it is possible to change the moving velocity of the viewpoint to the moving velocity of the ultrasonic probe 8.

In addition, the ultrasonic diagnostic apparatus 1 can execute rending processing based on the three-dimensional data generated in real time by using the absolute coordinate system defined by the position sensor 9. This makes it possible to display a perspective projection image at the viewpoint moving in the lumen at a constant velocity, after the movement of the ultrasonic probe 8, concerning the same living body tissue (for example, the lumen) as that in the three-dimensional data generated before the movement of the ultrasonic probe 8. This makes it possible to consecutively display the rendering images generated accompanying the movement of the viewpoint in real time.

In addition, the ultrasonic diagnostic apparatus 1 can maintain a viewpoint in rendering processing at the viewpoint set before the movement of the ultrasonic probe 8 even after the movement of the ultrasonic probe 8. It is also possible to combine before-movement three-dimensional data with after-movement three-dimensional data.

The apparatus can execute ultrasonic scanning again in response to when the viewpoint set immediately below the ultrasonic probe 8 on the absolute coordinate system reaches an end portion region of three-dimensional data. This makes it possible to display the rendering images generated accompanying the movement of the viewpoint at the current frame rate. In addition, it is possible to change ultrasonic transmission/reception conditions to those optimal for continuously displaying the lumen in accordance with the position of the viewpoint in an end portion region.

When the lumen branches, it is also possible to decide a viewpoint moving direction in accordance with the position and angle of the ultrasonic probe 8. In addition, it is possible to display the moving direction of the ultrasonic probe 8 on a body mark if the direction of the central line differs from the moving direction of the ultrasonic probe 8.

As described above, it is possible to display rendering images of the interior of a living body tissue without making them fall outside the interior of the living body tissue. For example, it is possible to display a perspective projection image of the interior of the lumen as an observation target without making it fall outside the lumen.

In addition, when the technical idea of the ultrasonic diagnostic apparatus 1 is to be implemented by a medical image processing apparatus as a modification of the above embodiment, for example, the apparatus includes the constituent elements in the solid line in the block diagram of FIG. 1. At this time, the processing concerning the perspective projection image generation function corresponds to the processing from step Sa5 to step Sa1. These processes are the same as in the embodiment. Note that the storage unit 31 stores three-dimensional data in step Sa5 in advance, together with probe position information (coordinates and angle). In addition, the storage unit 31 stores probe position information corresponding to the movement trace of the ultrasonic probe 8 in association with three-dimensional data. This makes it possible for the medical image processing apparatus to display rendering images of the interior of a living body tissue without making them fall outside the interior of the living body tissue by using the three-dimensional data acquired in the past and the movement trace of the probe.

In addition, the medical image processing apparatus can also execute the above processing by reading a DICOM file (e.g., three-dimensional data) output from the ultrasonic diagnostic apparatus. Furthermore, each function according to the embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus for generating perspective projection images corresponding to viewpoints which are set in a lumen of an object accompanying a movement of an ultrasonic probe, and for displaying the perspective projection images corresponding to the viewpoints, comprising:
the ultrasonic probe including a plurality of ultrasonic transducers and configured to be in contact with a body surface of the object;
a position detection sensor configured to detect first and second positions and a moving direction of the ultrasonic probe with reference to a predetermined common reference position, the second position representing a position of the ultrasonic probe with reference to the predetermined common reference position after movement of the ultrasonic probe;
a transducer configured to supply a driving signal to each of the ultrasonic transducers and generate a reception signal based on each received echo signal; and
a computer
configured to generate first three-dimensional data based on the received echo signal at the first position of the ultrasonic probe and second three-dimensional data based on the received echo signal at the second position of the ultrasonic probe;
configured to specify, with reference to the predetermined common reference position, a first luminal region in an inside of the lumen to be viewed from a first view point in the first three-dimensional data, and a first line of sight;
configured to generate a first perspective projection image of the first luminal region by perspective projection using at least a set of the first view point, the first line of sight and the first three-dimensional data;
configured to specify, with reference to the predetermined common reference position, a second luminal region in the inside of the lumen to be viewed from a second view point in the second three-dimensional data, and a second line of sight, the second view point being determined based on the moving direction of the ultrasonic probe, wherein
the first line of sight determined based on a direction along a first central line at the first view point of branches of the lumen, the second line of sight determined based on a direction along a second central line at the second view point of branches of the lumen, all of which are presented with reference to the predetermined common reference position, where the lumen branches at a branching portion in the lumen and has at least two branches represented by the first central line and the second central line; and
configured to generate a second perspective projection image of the second luminal region by perspective projection using at least a set of the second view point, the second line of sight and the second three-dimensional data.

2. The ultrasonic diagnostic apparatus of claim 1, wherein the computer is configured to set the second viewpoint based on the second position to coincide with the first viewpoint.

3. The ultrasonic diagnostic apparatus of claim 1, wherein the computer is configured to set a viewpoint setting region for setting the first viewpoint in the first three-dimensional data, and to set the first viewpoint in an intersection region between the lumen and the view point setting region.

4. The ultrasonic diagnostic apparatus of claim 1, further comprising a display monitor configured to display the perspective projection image,
wherein the computer is configured to set a lumen peripheral region having a predetermined thickness around a specified luminal region,
the position detection sensor is configured to detect the moving direction of the ultrasonic probe with reference to the predetermined common reference position,
the computer is configured to specify the lumen direction in the first luminal region in the first three-dimensional data, and to determine whether a plane perpendicular to the moving direction in the first three-dimensional data includes the lumen peripheral region, and the display monitor is configured to display the lumen direction when the lumen peripheral region falls outside the perpendicular plane.

5. The ultrasonic diagnostic apparatus of claim 1, wherein the computer is configured to set the second viewpoint by calculating inner products of a first vector representing the moving direction of the ultrasonic probe and second vectors representing the lumen directions.

6. The ultrasonic diagnostic apparatus of claim 1, wherein the computer is configured to generate combined three-dimensional data by combining the first three-dimensional data with the second three-dimensional data.

7. The ultrasonic diagnostic apparatus of claim 6, wherein the computer is configured to set the second viewpoint in the combined three-dimensional data, and
the computer is configured to generate the second perspective projection image by the perspective projection using at least the second viewpoint and the combined three-dimensional data.

8. The ultrasonic diagnostic apparatus of claim 1, wherein the computer is configured to set the first three-dimensional data and the second three-dimensional data on a same coordinate system having the predetermined common reference position as an origin, and to set positions of the first viewpoint and the second viewpoint with reference to the common reference position in the first luminal region and the second luminal region specified in the first three-dimensional data and the second three-dimensional data.

9. The ultrasonic diagnostic apparatus of claim 8, wherein the same coordinate system comprises an absolute coordinate system.

10. The ultrasonic diagnostic apparatus of claim 1, wherein the computer is configured to move the first viewpoint to the second luminal region in the second three-dimensional data at a velocity corresponding to a moving velocity of the ultrasonic probe.

11. The ultrasonic diagnostic apparatus of claim 10, wherein the computer is configured to control a timing to supply the driving signal to each of the ultrasonic transducers,
wherein the control unit is configured to control the transducer to supply the driving signal to each of the ultrasonic transducers, in response to the first viewpoint entering a predetermined region near an end portion of the first three-dimensional data.

12. The ultrasonic diagnostic apparatus of claim 11, wherein the control unit is configured to change ultrasonic transmission conditions based on a position of the first viewpoint in the predetermined region.

13. A medical image processing apparatus for generating perspective projection images corresponding to viewpoints which are set in a lumen of an object accompanying a movement of an ultrasonic probe, and for displaying the generated perspective projection images, comprising:
a storage configured to store a first three-dimension data acquired at a first position of the ultrasonic probe with reference to a predetermined common reference position as detected by a position detection sensor,
Wherein the storage further configured to store a second three-dimension data acquired at a second position of the ultrasonic probe with reference to the predetermined common reference position as detected by the position detection sensor, wherein the ultrasonic probe contacts a body surface of the object; and
a computer;
configured to specify, with reference to the predetermined common reference position, a first luminal region in an inside of the lumen to be viewed from a first view point in the first three-dimensional data, and a first line of sight
configured to generate a first perspective projection image of the first luminal region by perspective projection using at least a set of the first view point, the first line of sight and the first three-dimensional data;
configured to specify, with reference to the predetermined common reference position, a second luminal region in the inside of the lumen to be viewed from a second view point in the second three-dimensional data, and a second line of sight, the second view point being determined based on a moving direction of the ultrasonic probe, wherein
the first line of sight determined based on a direction along a first central line at the first view point of branches of the lumen, the second line of sight determined based on a direction along a second central line at the second view point of branches of the lumen, all of which are presented with reference to the predetermined common reference position, where the lumen branches at a branching portion in the lumen and has at least two branches represented by the first central line and the second central line; and
configured to generate a second perspective projection image of the second luminal region by perspective projection using at least a set of the second view point, the second line of sight and the second three-dimensional data.

14. The medical image processing apparatus of claim 13, wherein the computer is configured to set the second viewpoint by calculating inner products of a first vector representing the moving direction of the ultrasonic probe and second vectors representing the lumen directions.

15. The medical image processing apparatus of claim 13, wherein the computer is configured to set the first three-dimensional data and the second three-dimensional data on a same coordinate system having the predetermined common reference position as an origin, and to set positions of the first viewpoint and the second viewpoint with reference to the common reference position in the first luminal region and the second luminal region specified in the first three-dimensional data and the second three-dimensional data, respectively.

16. The medical image processing apparatus of claim 15, wherein the same coordinate system comprises an absolute coordinate system.

17. A medical image processing method for generating perspective projection images corresponding to viewpoints which are set in a lumen of an object accompanying a movement of an ultrasonic probe, and for displaying the generated perspective projection images, comprising a computer to perform the steps of: generating a first three-dimensional data based on received echo signal at a first position of the ultrasonic probe and second three-dimensional data based on received echo signal at a second position of the ultrasound probe; specifying, with reference to a predetermined common reference position, a first luminal region in an inside the lumen to be viewed from a first view point in the first three-dimensional data, and a first line of sight;
generating a first perspective projection image of the first luminal region by perspective projection using at least a set of the first view point, the first line of sight and the first three-dimensional data;
specifying, with reference to the predetermined common reference position, a second luminal region in the inside of the lumen to be viewed from a second view point in the second three-dimensional data, and a second line of sight, the second view point being determined based on a moving direction of the ultrasonic probe, wherein the first line of sight determined based on a direction along a first central line at the first view point of branches of the lumen, the second line of sight determined based on a direction along a second central line at the second view point of branches of the lumen, all of which are presented with reference to the predetermined common reference position, where the lumen branches at a branching portion in the lumen and has at least two branches represented by the first central line and the second central line; and generating a second perspective projection image of the second luminal region by perspective projection using at least a set of the second view point, the second line of sight and the second three-dimensional data.

18. The medical image processing method of claim 17, wherein the second viewpoint is calculated by inner products of a first vector representing the moving direction of the ultrasonic probe and second vectors representing the lumen directions.

19. The medical image processing method of claim 17, further comprising setting the first three-dimensional data and the second three-dimensional data on a same coordinate system having the predetermined common reference position as an origin, and setting positions of the first viewpoint and the second viewpoint with reference to the common reference position in the first luminal region and the second luminal region specified in the first three-dimensional data and the second three-dimensional data, respectively.

20. The medical image processing method of claim 19, wherein the same coordinate system comprises an absolute coordinate system.

* * * * *